(12) United States Patent
Bergmeister, III et al.

(10) Patent No.: US 7,199,076 B2
(45) Date of Patent: Apr. 3, 2007

(54) METHODS OF MAKING AND USING A SELECTIVE HYDROGENATION CATALYST

(75) Inventors: Joseph Bergmeister, III, Kingwood, TX (US); Tin-Tack Peter Cheung, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 42 days.

(21) Appl. No.: 10/741,800

(22) Filed: Dec. 19, 2003

(65) Prior Publication Data

US 2005/0137433 A1 Jun. 23, 2005

(51) Int. Cl.
*B01J 27/06* (2006.01)
*B01J 27/128* (2006.01)
*B01J 27/13* (2006.01)
*B01J 27/138* (2006.01)

(52) U.S. Cl. ............... 502/224; 502/226; 502/227; 502/229; 502/230

(58) Field of Classification Search ............... 502/224, 502/229, 230, 227, 226
See application file for complete search history.

(56) References Cited

U.S. PATENT DOCUMENTS

| | | | | |
|---|---|---|---|---|
| 2,802,889 | A | 8/1957 | Frevel et al. ............... | 260/677 |
| 3,325,556 | A | 6/1967 | De Rosset ................... | 260/677 |
| 4,113,970 | A | 9/1978 | Tanabe et al. ............... | 560/244 |
| 4,404,124 | A | 9/1983 | Johnson et al. ............. | 252/466 |
| 4,484,015 | A | 11/1984 | Johnson et al. ............. | 585/262 |
| 5,059,731 | A | 10/1991 | Berrebi ....................... | 585/259 |
| 5,475,173 | A | 12/1995 | Cheung et al. ............. | 585/259 |
| 5,488,024 | A | 1/1996 | Cheung et al. ............. | 502/325 |
| 5,489,565 | A | 2/1996 | Cheung et al. ............. | 502/325 |
| 5,510,550 | A | 4/1996 | Cheung et al. ............. | 585/259 |
| 5,583,274 | A | 12/1996 | Cheung et al. ............. | 585/261 |
| 5,585,318 | A | 12/1996 | Johnson et al. ............. | 502/330 |
| 5,587,348 | A | 12/1996 | Brown et al. ................ | 502/230 |
| 5,648,576 | A | 7/1997 | Nguyen Than et al. ..... | 585/260 |
| 5,698,752 | A | 12/1997 | Brown et al. ................ | 585/260 |
| 5,889,187 | A | 3/1999 | Nguyen Than et al. ..... | 585/260 |
| 6,054,409 | A | 4/2000 | Nguyen Thanh et al. ... | 502/330 |
| 6,084,140 | A | 7/2000 | Kitamura et al. ........... | 585/260 |
| 6,096,933 | A | 8/2000 | Cheung et al. | |
| 6,127,310 | A | 10/2000 | Brown et al. ................ | 502/339 |
| 6,127,588 | A | 10/2000 | Kimble et al. ............... | 585/260 |
| 6,350,717 | B1 | 2/2002 | Frenzel et al. .............. | 502/330 |
| 6,417,136 | B2 | 7/2002 | Cheung et al. ............. | 502/330 |
| 6,437,206 | B1 | 8/2002 | Meyer et al. ................ | 585/260 |
| 2001/0001805 | A1 | 5/2001 | Brown et al. ................ | 585/259 |
| 2004/0192983 | A1* | 9/2004 | Bergmeister et al. ....... | 585/259 |

FOREIGN PATENT DOCUMENTS

| | | |
|---|---|---|
| DE | 3312252 | 10/1984 |
| EP | 0722776 A1 | 7/1996 |
| EP | 0792685 A1 | 9/1997 |
| EP | 0689872 B1 | 8/2001 |
| FR | 2720956 | 6/1994 |
| WO | WO 99/46041 | 9/1999 |
| WO | WO 2004/074220 | 9/2004 |

OTHER PUBLICATIONS

Park, et al., "Promotional Effects of Potassium on Pd/Al$_2$O$_3$ Selective Hydrogenation Catalysts," *Ind. Eng. Chem. Res.*, 1992, 31, pp. 469-474, no month.
Park, et al., "Potassium Promoter for Palladium on Alumina Selective Hydrogenation Catalysts," *Journal of Chemical Society, Chemical Communications*, 1991, pp. 1188-1189, no month.
Boitiaux, et al., "Newest Hydrogenation Catalysts," *Hydrocarbon Processing*, Mar. 1985, pp. 51-59.
PCT International Search Report, PCT/US2004/041612, Mar. 23, 2005.

* cited by examiner

*Primary Examiner*—Elizabeth D. Wood
(74) *Attorney, Agent, or Firm*—Rodney B. Carroll; K. KaRan Reed; David W. Dockter (57) ABSTRACT

In an embodiment, a method of hydrogenating a highly unsaturated hydrocarbon to an unsaturated hydrocarbon includes contacting the highly unsaturated hydrocarbon with a catalyst in the presence of hydrogen. The catalyst comprises palladium and an inorganic support having a surface area of from about 4.5 to about 20 m$^2$/g, or alternatively 5 to 14.5 m$^2$/g. The inorganic support may comprise α-alumina treated with a fluoride source. The palladium may be primarily disposed near the surface of the support. In addition, the catalyst may comprise silver distributed throughout the support. In another embodiment, a method of making the foregoing selective hydrogenation catalyst includes contacting a fluorine-containing compound with an inorganic support, heating the support, and adding palladium to the inorganic support. After adding palladium to the support, the support can then be heated again, followed by adding silver to and then heating the support once again.

50 Claims, 4 Drawing Sheets

METHODS OF MAKING AND USING A SELECTIVE HYDROGENATION CATALYST

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present invention relates to the production of monoolefins, and more particularly to methods of making a catalyst and using the same to selectively hydrogenate highly unsaturated hydrocarbons, e.g., acetylene, contained within an unsaturated hydrocarbon stream to monoolefins.

BACKGROUND OF THE INVENTION

Monoolefins such as ethylene and propylene are often employed as feedstocks in preparing value added chemicals and polymers. Monoolefins may be produced by pyrolysis or steam cracking of naphtha, refinery gases, ethane, propane, butane, and the like. Monoolefins produced in this manner usually contain small proportions of acetylenes and diolefins that adversely affect production of subsequent chemicals and polymers. Thus, to form a polymer grade monoolefin, the amount of acetylenes and diolefins recovered in a monoolefin stream is typically reduced. For example, in polymer grade ethylene, it is generally preferred that the acetylene content be less than about 2 ppm, more preferably less than about 1 ppm.

One technique commonly used to reduce the amount of acetylenes and diolefins (i.e., highly unsaturated hydrocarbons) in an unsaturated hydrocarbon stream primarily comprising monoolefins involves selectively hydrogenating the acetylenes and diolefins to monoolefins. This process is selective in that hydrogenation of the monoolefin and the highly unsaturated hydrocarbons to saturated hydrocarbons is minimized. For example, hydrogenation of ethylene to ethane and of acetylene to ethane is minimized. This technique may be performed using catalysts comprising palladium and an inorganic support. However, such catalysts can produce green oil by oligomerizing the acetylenes and diolefins in some circumstances. As used herein, green oil refers to molecules having more than 4 carbon atoms per molecule that undesirably foul the selective hydrogenation catalyst, causing the catalyst to deactivate. The deactivation of the selective hydrogenation catalyst results in the catalyst having a lower activity and selectivity to monoolefins. Green oil production is particularly apparent in backend hydrogenation reactors. As used herein, backend refers to the location of the hydrogenation reactors in an unsaturated hydrocarbon production unit downstream from a deethanizer that receives the higher boiling fraction from a demethanizer as feed. A selective hydrogenation catalyst in such backend reactors requires regular regeneration, and with each regeneration, the selectivity and the life of the catalyst decreases.

Therefore, a need exists for a selective hydrogenation catalyst that undergoes less fouling during the hydrogenation of acetylenes and diolefins, particularly in backend hydrogenation reactors. That is, it is desirable to produce less green oil, thereby extending the life of the catalyst and maintaining catalyst selectivity.

SUMMARY OF THE INVENTION

In an embodiment, a method of hydrogenating a highly unsaturated hydrocarbon to an unsaturated hydrocarbon includes contacting the highly unsaturated hydrocarbon with a catalyst in the presence of hydrogen at conditions effective to selectively hydrogenate the highly unsaturated hydrocarbon to the unsaturated hydrocarbon. The catalyst comprises palladium and an inorganic support having a surface area of from about 4.5 to about 20 $m^2/g$. The inorganic support may comprise α-alumina treated with a fluoride source. The palladium may be primarily disposed near the periphery of the support. In an embodiment, the palladium is primarily disposed within 400 microns of the periphery of the support. In addition, the catalyst may comprise silver distributed throughout the support such that a weight ratio of the silver to the palladium is from about 2 to about 10.

In another embodiment, a method of making the foregoing selective hydrogenation catalyst includes contacting a fluorine-containing compound with an inorganic support and heating the support. The fluoride-treated inorganic support may be washed to remove any residual materials therefrom before or after heating the support. Next, palladium may be added to the support. After adding palladium to the support, the support can then be heated again, followed by adding silver to and then heating the support once again.

In a further embodiment, a method of making the foregoing selective hydrogenation catalyst includes contacting a fluorine-containing compound with an inorganic support and heating the support. The fluoride-treated inorganic support may be washed to remove any residual materials therefrom before or after heating the support. Palladium may then be added to the support. After adding palladium to the support, the support can then be heated again, followed by adding silver to and then heating the support once again. Then an iodine precursor can be added to the support, followed by heating the support yet again to form a selective hydrogenation catalyst.

DESCRIPTION OF THE DRAWINGS

The invention, together with further advantages thereof, may best be understood by reference to the following description taken in conjunction with the accompanying drawings in which.

DETAILED DESCRIPTION OF THE INVENTION

In an embodiment, methods of making a catalyst for selectively hydrogenating highly unsaturated hydrocarbons to unsaturated hydrocarbons comprise contacting a fluorine-containing compound with an inorganic support, heating the inorganic support, and adding palladium to the inorganic support. The details of such methods are provided below. As used herein, a highly unsaturated hydrocarbon is defined as a hydrocarbon containing at least one triple bond or conjugated carbon-carbon double bond, and an unsaturated hydrocarbon is defined as a hydrocarbon containing an isolated carbon-carbon double bond. An example of a highly unsaturated hydrocarbon is acetylene, and an example of an unsaturated hydrocarbon is ethylene. Further, an unsaturated hydrocarbon is defined as a hydrocarbon containing one or more pair of carbon atoms linked together by a double bond. It is also understood that the term "catalyst" refers to the support together with the materials impregnated in or on the support.

An inorganic support having a surface area of from about 4.5 to about 20 $m^2/g$ may be employed for the catalyst. Alternatively, the support may have a surface area of from about 5 to about 14.5 $m^2/g$ or from about 5 to about 10 $m^2/g$. The surface area of the support may be determined using the well-known method of Brunauer, Emmett, and Teller ("BET") by measuring the quantity of nitrogen adsorbed on the catalyst. Alternatively, it can also be measured by mercury intrusion. A suitable mercury intrusion method is described in ASTM UOP 578-02, entitled "Automated Pore Volume and Pore Size Distribution of Porous Substances by MERCURY Porosimetry," which is incorporated by reference herein in its entirety. It is believed that using a support having a surface area in these ranges reduces the fouling rate and the selectivity of the resulting catalyst. The inorganic support may comprise, for example, alumina, silica, titania, zirconia, aluminosilicates (clays and/or zeolites), spinels such as zinc aluminate, zinc titanate, and magnesium aluminate, or combinations thereof. An example of a suitable inorganic support is an alpha($\alpha$)-alumina support.

The inorganic support may be contacted with a solution, e.g., an aqueous solution, comprising at least one fluorine-containing compound. The method used to contact the inorganic support with the fluorine-containing compound may be incipient wetness impregnation, which is well known in the art. During incipient wetness impregnation, the pores of the support become substantially filled with the fluorine-containing solution. The solution may contain a sufficient amount of fluorine-containing compound to form a catalyst having from about 10 to about 10,000 ppm by weight of the fluorine, alternatively from about 10 to about 8,000 ppm, or from about 10 to about 5,000 ppm. Examples of suitable fluorine-containing compounds include, but are not limited to, alkali metal fluoride, alkali metal bifluoride, hydrogen fluoride, ammonium fluoride, tetraalkylammonium fluoride (e.g., tetramethylammonium fluoride and tetraethylammonium fluoride), ammonium bifluoride, and combinations thereof. The fluorine-containing compound is desirably potassium fluoride. Without intending to be limited by theory, it is believed that the fluorine adsorbs on the inorganic support and reacts with hydroxyl groups proximate the surface of the support, thus filling at least a portion of the bonding sites in the support. As such, the fluorine can subsequently act as a blocking agent by inhibiting other species from filling those bonding sites.

The catalyst precursor formed by contacting the inorganic support with the fluorine-containing compound subsequently may be dried at a temperature of from about 50° C. to about 150° C. for about 0.5 hour to about 20 hours. The catalyst precursor further may be heated in an oxidizing atmosphere such as air at a temperature of from about 300° C. to about 800° C. for about 0.2 hour to about 20 hours. Before or after heating the catalyst precursor, it may be washed with, for example, water to remove any residual material/impurities that may have been introduced with the fluorine-containing compound.

Next, palladium may be added to the inorganic support by contacting the support with a solution, e.g., an aqueous solution, comprising palladium metal or a palladium-containing compound such as palladium chloride or palladium nitrate. The palladium-containing solution may contain a sufficient amount of palladium to form a catalyst having from about 0.01 to about 1.0 weight % palladium, alternatively from about 0.01 to about 0.8 weight % palladium, or from about 0.01 to about 0.5 weight % palladium, all weight percentages being by weight of the total catalyst. In an embodiment, the palladium is added to the support in a manner to cause at least 90 weight % of the catalyst particles to have the palladium concentrated near the periphery of the catalyst particles such that those particles have a so-called palladium skin. As used herein, the term "palladium skin" refers to the exterior layer of the inorganic support that contains substantially all of the palladium incorporated in the support. The skin can be any thickness as long as such thickness can promote the hydrogenation process disclosed herein. Generally, the thickness of the skin can be in the range of from about 1 micron to about 1,000 microns, from about 5 microns to about 750 microns, from about 5 microns to about 500 microns, or from about 10 microns to about 300 microns. In some embodiments, the skin thickness is less than about 1,000 microns, less than about 750 microns, less than about 500 microns, less than about 400 microns, or less than about 300 microns. Additional disclosure regarding the palladium skin can be found in U.S. Pat. Nos. 4,404,124 and 4,484,015, each of which is incorporated by reference herein in its entirety.

Suitable methods for determining the concentration of the palladium in the skin of the catalyst are known in the art. Determining the concentration of the palladium in the skin of the catalyst helps in determining the thickness of the skin. One technique that may be employed to determine the palladium skin thickness is the electron microprobe method. Another technique involves breaking open a representative sample of the catalyst particle and treating the catalyst particles with a dilute alcoholic solution of N,N-dimethyl-para-nitrosoaniline. The treating solution reacts with the palladium to give a red color that can be used to evaluate the distribution of the palladium. Yet another technique for measuring the concentration of the palladium in the skin of the catalyst involves breaking open a representative sample of catalyst particles, followed by treating the particles with a reducing agent such as hydrogen to change the color of the skin and thereby evaluate the distribution of the palladium.

Without intending to be limited by theory, it is believed that fluorine atoms bonded with surface hydroxyl groups of the inorganic support block the adsorption of palladium at neighboring sites. In this manner, the dispersion of the palladium within the skin is improved. It is believed that increasing the dispersion of the palladium results in a catalyst that produces less green oil, has a lower fouling rate, and deactivates at a lower rate.

The catalyst precursor formed by contacting the fluorine-containing inorganic support with the palladium-containing compound optionally may be dried at a temperature of from about 25° C. to about 150° C. for a period of from about 0.5 hour to about 20 hours. The catalyst precursor described above may optionally be further heated in an oxidizing atmosphere such as air at a temperature of from about 300° C. to about 800° C. for a period of from about 0.2 hour to about 20 hours.

A selectivity enhancer subsequently may be added to the inorganic support, followed by again drying and heating the inorganic support. Examples of suitable selectivity enhancers include, but are not limited to, silver, silver compounds, phosphorus, sulfur, phosphorus compounds, sulfur compounds, potassium, potassium compounds, and combinations thereof. Silver in the form of silver metal, or a silver compound such as silver nitrate is desirably added to the inorganic support. The resulting catalyst comprises from about 0.01 to about 10 weight % silver, alternatively from about 0.01 to about 5 weight % silver, or from about 0.01 to about 2 weight % silver, all weight percentages being based on a total weight of the catalyst.

In some embodiments, the selectivity enhancer can be distributed throughout the catalyst support using a method known to those skilled in the art. As an example, the catalyst precursor particles can be placed in an aqueous silver nitrate solution of a quantity greater than that necessary to fill the pore volume of the particles. The resulting catalyst may be dried and calcined to decompose the fluorine-, palladium-, and silver-containing compounds before using it in the hydrogenation process. As an example, this drying can be performed at a temperature in the range of from about 25° C. to about 150° C. for a period of from about 0.5 hour to about 20 hours. As an example, this calcining can be done at temperatures up to about 800° C., e.g., in the range of from about 150° C. to about 750° C., for a period of from about 0.2 to about 20 hours. Optionally, the calcining may be followed by a reduction step that utilizes hydrogen or a hydrogen containing feed, e.g., the feed stream of the selective hydrogenation process, to reduce the catalyst metals, thereby providing for optimum operation of the selective hydrogenation process. As an example, the reduction can be carried out at a temperature in the range of from about 25° C. to about 450° C.

Thereafter, an iodine-containing material may optionally be added to the inorganic support using, e.g., incipient wetness impregnation or soaking, and the support may again be dried. The concentration of iodine in the resulting catalyst may range from about 1 ppm to about 1,000 ppm by weight, alternatively from about 1 ppm to about 800 ppm by weight, or from about 1 ppm to about 500 ppm by weight. Examples of suitable iodine-containing materials include, but are not limited to, elemental iodine, ammonium iodide, potassium iodide, tetraalkylammonium iodide (e.g., tetramethylammonium iodide and tetraethylammonium iodide), potassium iodate, and ammonium iodate. The resulting catalyst can be dried and calcined to decompose, e.g., the fluorine-, palladium-, silver-, and iodine-containing materials, before using it in the hydrogenation process. As an example, this drying can be carried out at a temperature in the range of from about 25° C. to about 150° C. for a period of from about 0.5 hour to about 20 hours. As an example, this calcining can be done at temperatures up to about 800° C., e.g., in the range of from about 150° C. to about 700° C. The calcining may also be followed by a reduction step, which can be accomplished using the $H_2$ feed for the selective hydrogenation process. As an example, the reduction can be carried out at a temperature in the range of from about 25° C. to about 450° C. The iodine further reduces the deactivation rate of the resulting catalyst.

In an embodiment, a catalyst formed in accordance with the method described above comprises palladium, silver, optionally iodine, and an α-alumina support treated with fluorine and having a surface area of from about 4.5 to about 20 $m^2/g$ or alternatively from about 5 to about 14.5 $m^2/g$. In another embodiment, a catalyst for selectively hydrogenating highly unsaturated hydrocarbons to unsaturated hydrocarbons may be made in the same manner as described above except that the steps related to placing fluorine and iodine on the inorganic support may be removed. Thus, the resulting catalyst comprises palladium, silver, and an α-alumina support having a surface area of from about 4.5 to about 20 $m^2/g$, or alternatively from about 5 to about 14.5 $m^2/g$.

In embodiments, methods of using the previously described selective hydrogenation catalysts comprise contacting an unsaturated hydrocarbon stream primarily containing an unsaturated hydrocarbon but also containing a highly unsaturated hydrocarbon, e.g., acetylene, with such catalyst in the presence of hydrogen at conditions effective to selectively hydrogenate the highly unsaturated hydrocarbon to an unsaturated hydrocarbon, e.g., ethylene. As mentioned previously, the catalyst comprises palladium and an inorganic support having a surface area of from about 4.5 to about 20 $m^2/g$, alternatively from about 5 to about 14.5 $m^2/g$.

Figure 1:
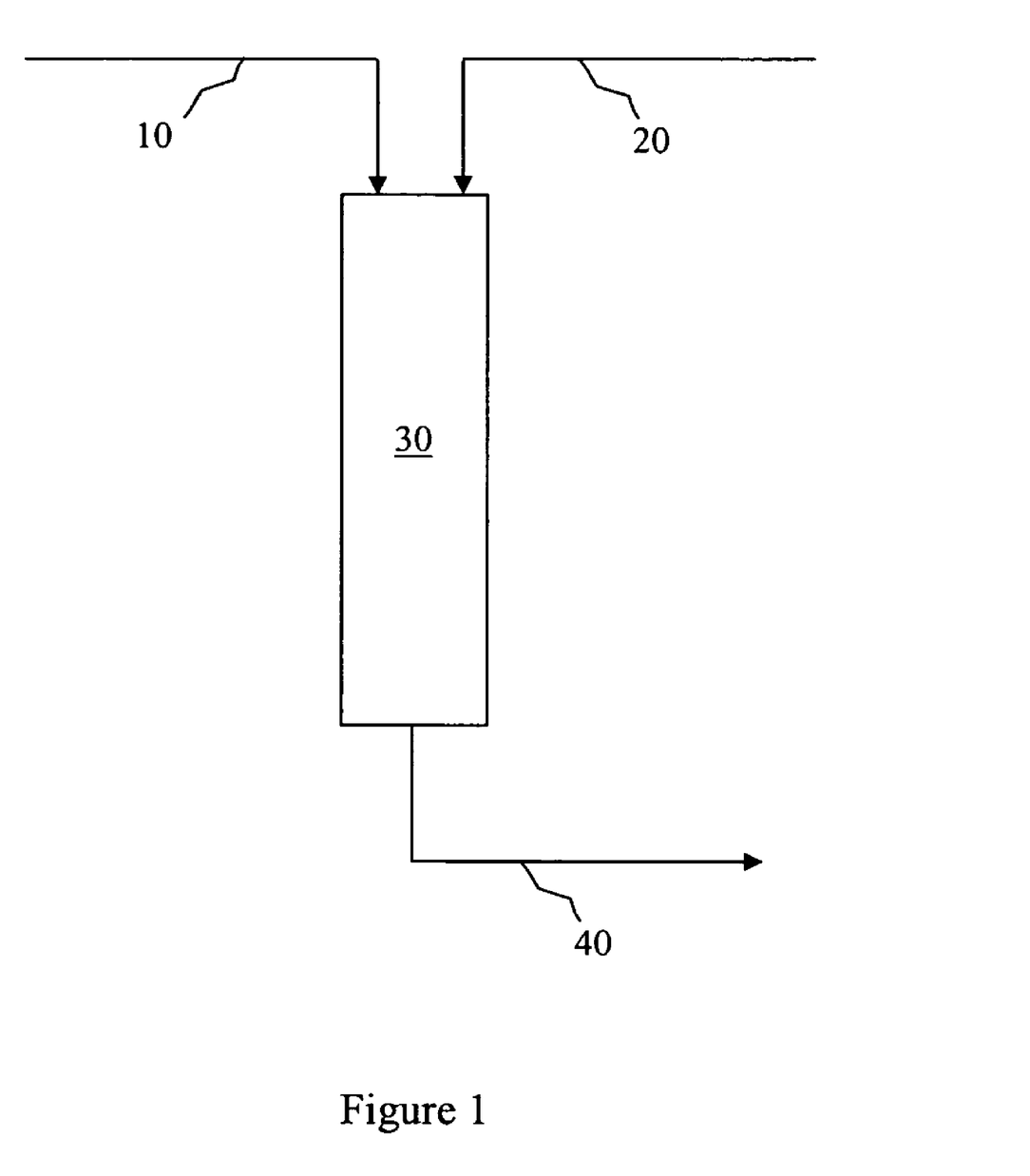
FIG. 1 depicts a process flow diagram of an embodiment in which an unsaturated hydrocarbon stream containing a highly unsaturated hydrocarbon is fed to a hydrogenation reactor for selective hydrogenation of the highly unsaturated hydrocarbon to a monoolefin.

FIG. 1 illustrates an embodiment of a hydrogenation process that utilizes a selective hydrogenation catalyst made in the manner described above. The hydrogenation process includes feeding an unsaturated hydrocarbon stream 10 and a hydrogen ($H_2$) stream 20 to a hydrogenation reactor 30 within which the selective hydrogenation catalyst is disposed. The unsaturated hydrocarbon stream 10 primarily comprises one or more unsaturated hydrocarbons, but it also contains one or more highly unsaturated hydrocarbons. Alternatively, unsaturated hydrocarbon stream 10 and hydrogen stream 20 may be combined in a single stream that is fed to hydrogenation reactor 30 (not shown). In an embodiment, reactor 30 is a backend hydrogenation reactor that may belong to a backend acetylene removal unit of an unsaturated hydrocarbon production plant. Accordingly, unsaturated hydrocarbon stream 10 may comprise hydrocarbons recovered from the overheads of a de-ethanizer, including one or more unsaturated hydrocarbons such as ethylene and one or more highly unsaturated hydrocarbons such as acetylene, which is a highly unsaturated hydrocarbon. The mole ratio of the hydrogen to the acetylene being fed to hydrogenation reactor 30 may be in the range of from about 0.1 to about 10, alternatively from about 0.5 to about 5, or from about 0.5 to about 3. It is understood that hydrogenation reactor 30 is not limited to use in backend acetylene removal units and may be used in any process deemed appropriate by one skilled in the art. In another embodiment, reactor 30 may represent a plurality of reactors separated by a means to remove heat produced by the reaction.

Carbon monoxide may also be fed to reactor 30 via a separate stream (not shown), or it may be combined with hydrogen stream 20. In an embodiment, the amount of carbon monoxide being fed to reactor 30 during the hydrogenation process is less than about 0.0015 mol % based on the total moles of fluid being fed to reactor 30. In alternative embodiments, unsaturated hydrocarbon stream 10 may include other highly unsaturated hydrocarbons in addition to acetylene, such as methylacetylene, vinylacetylene, ethylacetylene, 2-butyne, propadiene, butadiene, isoprene, 1,3-pentadienes, cyclopentadiene, and combinations thereof.

Hydrogenation reactor 30 may be operated at conditions effective to selectively hydrogenate highly unsaturated hydrocarbons to one or more monoolefins upon contacting the selective hydrogenation catalyst in the presence of the hydrogen. The conditions are desirably effective to maximize hydrogenation of highly unsaturated hydrocarbons to monoolefins and to minimize hydrogenation of highly unsaturated hydrocarbons to alkanes. As used herein, a monoolefin is defined as an unsaturated hydrocarbon containing one pair of carbon atoms linked together by a double bond, and an alkane is defined as a saturated hydrocarbon containing carbon atoms linked together only by single bonds. By way of example, acetylene may be selectively hydrogenated to ethylene. The temperature within the hydrogenation zone may be, for example, in the range of from about 5° C. to about 300° C., alternatively from about 10° C. to about 250° C., or from about 15° C. to about 200° C. Further, the pressure within the extraction-hydrogenation zone may be, for example, in the range of from about 15 to about 2,000 pounds per square inch gauge (psig), alternatively from about 50 to about 1,500 psig, or from about 100 to about 1,000 psig.

The selective hydrogenation catalyst may be arranged in any suitable configuration within hydrogenation reactor 30, such as a fixed catalyst bed. Prior to performing the hydrogenation process, the metals in the selective hydrogenation catalyst may be reduced by, for example, exposing the catalyst to a hydrogen-containing gas at a temperature of from about 25° C. to about 450° C. Without intending to be limited by theory, it is believed that due to the increased dispersion of palladium in the catalyst and/or the particular surface area of the catalyst support, the fouling rate of the catalyst is reduced, the amount of green oil produced is reduced, and/or the selectivity of the catalyst to monoolefins is increased. As a result, the life of the catalyst is extended such that the catalyst requires regeneration less often, resulting in lower operating costs of the hydrogenation process.

Referring back to FIG. 1, an effluent stream 40 comprising unsaturated hydrocarbons, including the one or more monoolefins produced in hydrogenation reactor 30, and any unconverted reactants exit hydrogenation reactor 30. In an embodiment, effluent stream 40 primarily comprises ethylene and contains less than about 5 ppm, desirably less than about 1 ppm of highly unsaturated hydrocarbons.

The catalyst contained in hydrogenation reactor 30 may be regenerated as needed. Regeneration of the catalyst may be accomplished by, for example, heating the catalyst in the presence of air at a temperature not in excess of about 500° C. to burn off any organic matter, polymer, or char.

EXAMPLES

The invention having been generally described, the following examples exemplify embodiments of the invention and to demonstrate the practice and advantages thereof. It is understood that the examples are given by way of illustration and are not intended to limit the specification or the claims to follow in any manner. All numerical values are approximate. When numerical ranges are given, it should be understood that embodiments outside the stated ranges may still fall within the scope of the invention. Specific details described in each example should not be construed as necessary features of the invention.

In the following examples, the amount of green oil produced by each catalyst sample was calculated as follows:

% weight gain/day (i.e., green oil made)=(((final catalyst weight–initial catalyst weight)/initial catalyst weight)/days)*100

Further, the selectivity to ethylene was also calculated using the following set of equations, where "$C_4$" represents butane and butenes and where "heavies" refer to hydrocarbons having more carbon atoms than $C_4$:

selectivity to ethane=(weight of ethane made/weight of acetylene consumed)*100 selectivity to $C_4$'s=(weight of $C_4$'s made/weight of acetylene consumed)*100 selectivity to heavies=(weight of heavies made/weight of acetylene consumed)*100 selectivity (sel.) to ethylene=100–sel. to ethane–sel. to $C_4$'S–sel. to heavies In addition, the deactivation rate of the catalyst was determined as being the absolute value of the change in conversion per given time.

Example 1

This example illustrates the preparation of various palladium-containing catalyst samples and the use of the samples in a hydrogenation process. Catalyst sample A, which served as a control, was a commercial catalyst comprising Pd and Ag supported on $\alpha$-$Al_2O_3$. It was available in the form of 4 mm×4 mm tablets and had a surface area of about 3.75 $m^2$/g. Catalyst sample A contained 0.018 wt. % Pd, 0.11 wt. % Ag, and about 99 wt. % $Al_2O_3$, all by weight of the total catalyst. This sample was obtained from Süd Chemie, Inc. of Louisville, Ky.

Catalyst sample B, which also served as a control, was prepared on $\alpha$-$Al_2O_3$ pellets purchased from Süd Chemie, Inc. The pellets were 4 mm×4 mm in size and had a surface area of 4.93 $m^2$/g. Catalyst sample B contained 0.02 wt. % Pd, 0.12 wt. % Ag, and about 99 wt. % $Al_2O_3$, all by weight of the total catalyst. A description of the preparation of catalyst sample B can be found in U.S. Pat. No. 4,484,015, which is incorporated by reference herein in its entirety.

Catalyst sample C was prepared by initially adding an aqueous solution containing 0.061 g KF in 75 g of distilled water to 300 g of the same $\alpha$-$Al_2O_3$ pellets used in catalyst sample B, followed by drying at 125° C. for 1 hour. The resulting support was washed 3 times with 300 mL of boiling distilled water. The support was then dried at 125° C. for 1 hour and calcined at 538° C. for three hours in air. Next palladium and silver were added to the support as described in U.S. Pat. No. 4,484,015. The final catalyst contained 0.02 wt. % Pd, 0.12 wt. % Ag, 0.0065 wt. % F, and about 99 wt. % $Al_2O_3$, all by weight of the total catalyst.

Catalyst sample D was prepared by first adding an aqueous solution containing 0.012 g $NH_4F$ in 25 g of distilled water to 100 g of the same $\alpha$-$Al_2O_3$ pellets used in catalyst sample B. The support was then dried at 125° C. for 1 hour and calcined at 538° C. for three hours in air. Next palladium and silver were added to the support as described in U.S. Pat.

No. 4,484,015. The final catalyst contained 0.02 wt. % Pd, 0.12 wt. % Ag, 0.0062 wt. % F, and about 99 wt. % $Al_2O_3$, all by weight of the total catalyst.

Catalyst sample E was prepared in the same manner as catalyst sample D, except that it contained 0.02 wt. % Pd, 0.12 wt. % Ag, 0.06 wt. % F, and about 99 wt. % $Al_2O_3$, all by weight of the total catalyst.

Each of the above catalyst samples was then subjected to the following procedure. About 20 mL of the sample was mixed with 40 mL of 14 grit alundum and placed in a stainless steel jacketed reactor tube having a 0.692 inch inner diameter and a length of about 36 inches. The catalyst resided in the middle of the reactor and both ends of the reactor were packed with about 40 mL of alundum. The reaction temperature was controlled by circulating ethylene glycol through the jacket of the reactor tube. The catalyst was then activated with $H_2$ (200 mL/min at atmospheric pressure and 170° F.) for 2 hours.

The catalyst was subsequently contacted with about 915 mL/min of a feed gas at 200 psig. The feed gas contained about 13 wt. % methane, 85.7 wt. % ethylene, 1.2 wt. % acetylene, and 0.1 wt. % hydrogen, all by weight of the total feed. The reaction temperature was adjusted to yield an acetylene conversion of about 80%, wherein conversion refers to the disappearance of acetylene. When the conversion of acetylene fell below a critical value, usually about 60%, the temperature was increased to reestablish about 80% conversion. The reactor exit gas was analyzed by gas chromatography using a $KCl$—$Al_2O_3$ plot column.

Tables 1 and 2 below summarize the results of running the above hydrogenation reaction for each catalyst sample. Catalyst sample A (3.75 m²/g) had a surface area less than the other catalyst samples (4.93 m²/g).

Based on the results shown in Table 1, the catalyst samples having a support surface area of at least about 5 m²/g (samples C and D) yielded a much higher conversion of acetylene and selectivity to ethylene, produced less green oil, and deactivated at a lower rate than the catalyst sample having a support surface area of less than 5 m²/g. As shown in Table 1 and 2, adding fluoride to the alumina support (samples C–E) greatly reduced the formation of green oil and lowered the deactivation rate of the catalyst.

Example 2

A control catalyst sample F was prepared in the same manner as catalyst sample B in Example 1. Also, three catalyst samples G, H, and I were prepared in the same manner as catalyst sample D in Example 1 but with varying amounts of fluorine: 0.006 wt. % F, 0.06 wt. % F, and 0.6 wt. % F, respectively. All of the catalyst samples contained 0.02 wt. % Pd and 0.12 wt. % Ag loaded on an $\alpha$-$Al_2O_3$ support having a surface area of about 5 m²/g. All of the previous weight percentages are by weight of the total catalyst. The catalyst samples F–I were then subjected to the same hydrogenation procedure as the samples in Example 1. Again, the temperature was set to provide for about 80% conversion of the acetylene, and as the conversion dropped over time to about 60%, the temperature was raised. This adjustment of the temperature was repeated as needed. Fouling rates were calculated at 80% conversion. A plot of temperature as a function of time was made for data taken at 80% conversion. Then the slope of that line was used to calculate the fouling rate.

Figure 2:
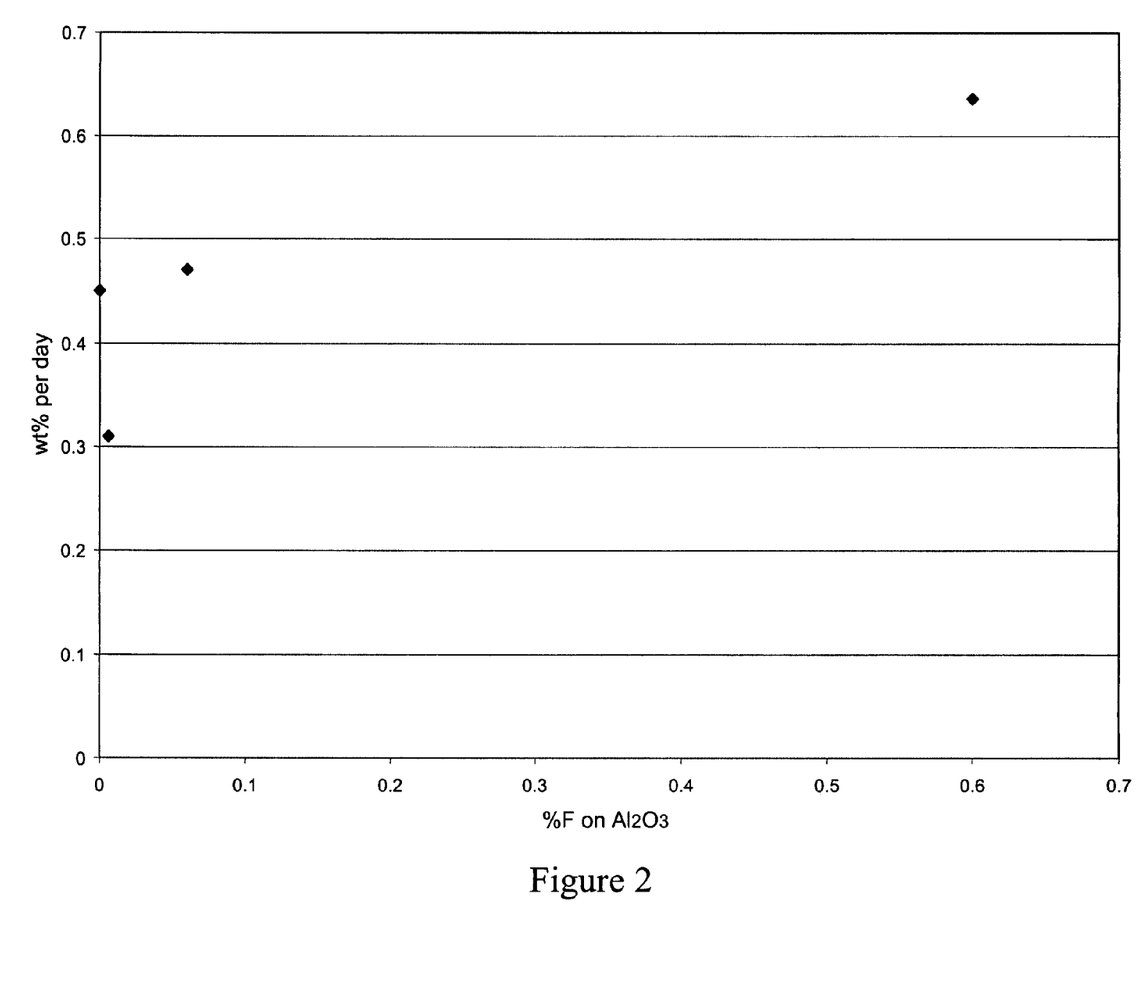
FIG. 2 is a graph of the amount of green oil formed per day during the hydrogenation of acetylene as a function of the amount of fluorine on a selective hydrogenation catalyst comprising palladium, silver, and fluorine supported by α alumina.
Figure 3:
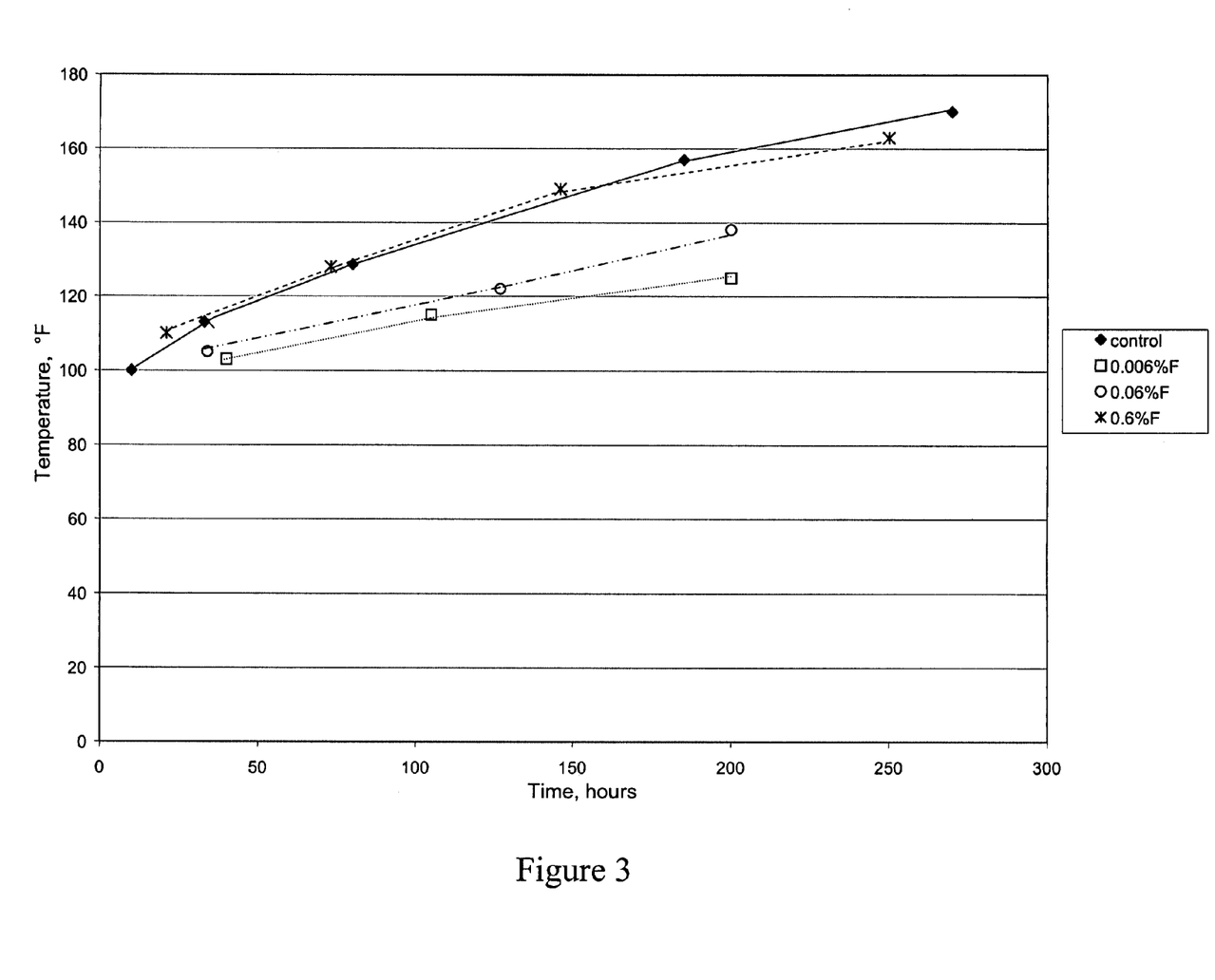
FIG. 3 is a graph of the reaction temperature for the hydrogenation of acetylene as a function of time, which illustrates the effect of adding $NH_4F$ before palladium and silver to the catalyst on the fouling rate at 80% conversion of the acetylene.
Figure 4:
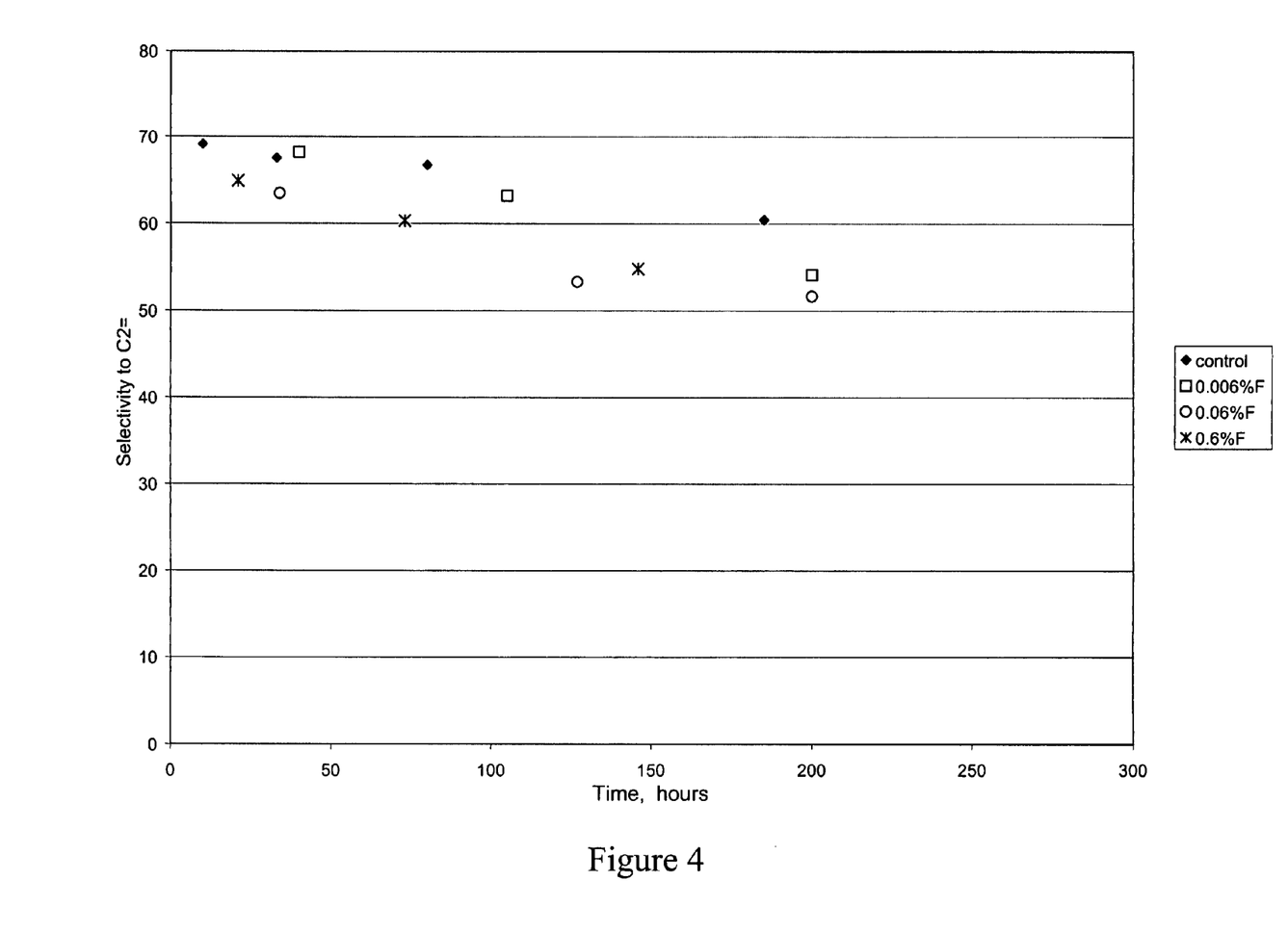
FIG. 4 is a graph of selectivity to ethylene as a function of time.

Table 3 below illustrates the effect of adding $NH_4F$ before Pd and Ag to the $\alpha$-$Al_{2O3}$ support on the catalyst's % weight gain/day (green oil formation), fouling rate, and selectivity to ethylene. FIG. 2 shows a plot of the % weight gain/day as a function of the amount of fluorine on the catalyst. In addition, FIG. 3 shows a plot of the reaction temperature as a function of time, illustrating the effect of adding $NH_4F$ before Pd and Ag on the fouling rate at 80% conversion of the acetylene. Further, FIG. 4 shows a plot of the selectivity to ethylene as a function of time.

TABLE 1

| Catalyst Sample | Reduction Temp., ° F. | Green Oil Made, % weight gain/day | Time on Test[a], hours | Time[b], hours | Conversion, % | Selectivity to Ethylene | Reaction Temp., ° F. | Deactivation, %/day |
|---|---|---|---|---|---|---|---|---|
| A(control) | 400 | 0.58 | 339 | 200 | 79 | 45 | 130 | 0.19 |
| C | 400 | 0.19 | 859 | 179 | 78 | 57 | 136 | 0.11 |
| D | 400 | 0.31 | 339 | 200 | 80 | 54 | 125 | 0.17 |

[a]total time of test
[b]time at which the conversion, selectivity, and reaction temperature was observed.

TABLE 2

| Cataylst Sample | Reduction Temp., ° F. | Green Oil Made, % weight gain/day | Time on Test[a], hours | Time[b], hours | Conversion, % | Selectivity, % | Reaction Temp., ° F. | Deactivation, %/day |
|---|---|---|---|---|---|---|---|---|
| B(control) | 170 | 0.45 | 341 | 195 | 78 | 61 | 157 | 0.27 |
| C | 170 | 0.21 | 1285 | 252 | 77 | 52 | 134 | 0.10 |
| E | 170 | 0.47 | 318 | 202 | 78 | 53 | 138 | 0.15 |

[a]total time of test
[b]time at which the conversion, selectivity, and reaction temperature was observed.

TABLE 3

| Catalyst Sample | Fluorine Concentration, wt. % | Green Oil Made, % weight gain/day | Fouling Rate, °F./hour | Selectivity to Ethylene[a], % |
|---|---|---|---|---|
| F(control) | 0 | 0.45 | 0.289 | 60 |
| G | 0.006 | 0.31 | 0.138 | 54 |
| H | 0.06 | 0.47 | 0.199 | 52 |
| I | 0.6 | 0.64 | 0.312 | 51 |

[a]selectivities were determined at 200 hours

Based on the results of this example, the catalyst sample having a small amount of fluorine (i.e., 0.006 wt. %) produced the least amount of green oil. Further, the fouling rate was much lower for the samples containing low levels of fluorine (i.e., 0.006 wt. % and 0.06 wt. %) compared to control sample F. The selectivity exhibited by catalyst sample G was similar to or slightly lower than that of control sample F, and the selectivities exhibited by catalyst samples H and I were slightly lower than or equivalent to that of catalyst sample G.

Example 3

This example illustrates the effect of surface area on Pd/Ag catalysts. Catalysts J, K, L, and M were prepared in the same manner as catalyst sample B in Example 1. Catalyst samples J–M contained about 99 wt. % $Al_2O_3$ and 0.02 wt. % Pd, all by weight of the total catalyst, and they had a Ag to Pd weight ratio of 5 to 6. As shown in Table 4 below, the catalyst samples J–M differed by their surface areas. The catalyst samples J–M were subjected to the same hydrogenation procedure as the samples in Example 1, with one noted exception: the conversion was held at 90% throughout the run. The run was stopped at about 210 hours or when the selectivity to ethylene reached zero.

The fouling rate was determined by plotting reaction temperature as a function of time for each sample and then taking the slope of that line. A selectivity comparison was also made by plotting the selectivity to ethylene as a function of time for each sample and then integrating the curve from 0 to 200 hours. Table 4 below shows these fouling rate and selectivity values.

TABLE 4

| Catalyst Sample | Surface Area[a], m²/g | Fouling Rate, °F./hour | Area under Selectivity curve[b] | Green Oil Made, % weight gain/day |
|---|---|---|---|---|
| J | 3.93 | 0.307 | 1.67 | 0.38 |
| K | 4.93 | 0.125 | 2.29 | 0.65 |
| L | 14.52 | 0.247 | 2.22 | 0.55 |
| M | 37.7 | 0.406 | 1 | 0.92 |

[a]determined by nitrogen BET
[b]all area values were ratioed to the smallest value This example shows that the optimal surface area of the support is in the range of from about 4.9 to about 14.5 m²/g. This range of surface area improved both the fouling rate and the selectivity of the catalyst.

While the preferred embodiments of the invention have been shown and described, modifications thereof can be made by one skilled in the art without departing from the spirit and teachings of the invention. The embodiments described herein are exemplary only and are not intended to be limiting. Many variations and modifications of the invention disclosed herein are possible and are within the scope of the invention. Use of the term "optionally" with respect to any element of a claim is intended to mean that the subject element is required, or alternatively, is not required. Both alternatives are intended to be within the scope of the claims.

Accordingly, the scope of protection is not limited by the description set out above, but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method of forming a catalyst, comprising:
   (a) contacting an alkali metal fluoride compound with an inorganic support;
   (b) heating the inorganic support;
   (c) washing the resulting solid from step (b) to remove any residual material introduced by the alkali metal fluoride compound; and
   (d) adding palladium to the inorganic support.

2. The method of claim 1, wherein step (b) is performed at a temperature of from about 300° C. to about 800° C. for about 0.2 hour to about 20 hours.

3. The method of claim 1, further comprising heating the inorganic support after performing step (c), (d), or both.

4. The method of claim 3, further comprising adding silver to the inorganic support and thereafter heating the support.

5. The method of claim 4, further comprising adding an iodine containing material to the inorganic support and thereafter heating the support.

6. The method of claim 1, wherein the support has a surface area of from about 4.5 to about 20 m²/g.

7. The method of claim 1, wherein the support has a surface area of from about 5 to about 14.5 m²/g.

8. The method of claim 1, wherein the inorganic support comprises alumina, silica, titania, zirconia, aluminosilicates, spinels, zinc aluminate, zinc titanate, and magnesium aluminate, or combinations thereof.

9. The method of claim 1, wherein the inorganic support comprises α-alumina.

10. The method of claim 1, wherein the catalyst comprises from about 10 to about 10,000 ppm by weight of fluorine.

11. The method of claim 1, wherein the catalyst comprises from about 10 to about 8,000 ppm by weight of fluorine.

12. The method of claim 1, wherein the catalyst comprises from about 10 to about 5,000 ppm by weight of fluorine.

13. The method of claim 1, wherein the catalyst comprises from about 0.01 to about 1.0 weight % palladium based on a total weight of the catalyst.

14. The method of claim 1, wherein the catalyst comprises from about 0.01 to about 0.8 weight % palladium based on a total weight of the catalyst.

15. The method of claim 1, wherein the catalyst comprises from about 0.01 to about 0.5 weight % palladium based on a total weight of the catalyst.

16. The method of claim 1, wherein the catalyst comprises from about 0.01 to about 10 weight % silver based on a total weight of the catalyst.

17. The method of claim 1, wherein the catalyst comprises from about 0.01 to about 5 weight % silver based on a total weight of the catalyst.

18. The method of claim 1, wherein the catalyst comprises from about 0.01 to about 2 weight % silver based on a total weight of the catalyst.

19. The method of claim 1, wherein the catalyst comprises from about 1 ppm by weight to about 1,000 ppm by weight of iodide.

20. The method of claim 1, wherein the catalyst comprises from about 1 ppm by weight to about 800 ppm by weight of iodide.

21. The method of claim 1, wherein the catalyst comprises from about 1 ppm by weight to about 500 ppm by weight of iodide.

22. A catalyst formed by the method of claim 1.

23. A method of forming a catalyst, comprising:
(a) contacting hydrogen fluoride, ammonium fluoride, tetraalkylammonium fluoride, ammonium bifluoride, or combinations thereof with an inorganic support;
(b) heating the inorganic support; and
(c) adding palladium to the inorganic support, wherein the catalyst is substantially free of a cation of an alkali metal compound.

24. The method of claim 23, wherein step (b) is performed at a temperature of from about 300° C. to about 800° C. for about 0.2 hour to about 20 hours.

25. The method of claim 23, further comprising heating the inorganic support after performing step (c).

26. The method of claim 25, further comprising adding silver to the inorganic support and thereafter heating the support.

27. The method of claim 26, further comprising adding an iodine containing material to the inorganic support and thereafter heating the support.

28. The method of claim 23, wherein the support has a surface area of from about 4.5 to about 20 m²/g.

29. The method of claim 23, wherein the support has a surface area of from about 5 to about 14.5 m²/g.

30. The method of claim 23, wherein the inorganic support comprises alumina, silica, titania, zirconia, aluminosilicates, spinels, zinc aluminate, zinc titanate, and magnesium aluminate, or combinations thereof.

31. The method of claim 23, wherein the inorganic support comprises α-alumina.

32. The method of claim 23, wherein the catalyst comprises from about 10 to about 10,000 ppm by weight of fluorine.

33. The method of claim 23, wherein the catalyst comprises from about 10 to about 8,000 ppm by weight of fluorine.

34. The method of claim 23, wherein the catalyst comprises from about 10 to about 5,000 ppm by weight of fluorine.

35. The method of claim 23, wherein the catalyst comprises from about 0.01 to about 1.0 weight % palladium based on a total weight of the catalyst.

36. The method of claim 23, wherein the catalyst comprises from about 0.01 to about 0.8 weight % palladium based on a total weight of the catalyst.

37. The method of claim 23, wherein the catalyst comprises from about 0.01 to about 0.5 weight % palladium based on a total weight of the catalyst.

38. The method of claim 23, wherein the catalyst comprises from about 0.01 to about 10 weight % silver based on a total weight of the catalyst.

39. The method of claim 23, wherein the catalyst comprises from about 0.01 to about 5 weight % silver based on a total weight of the catalyst.

40. The method of claim 23, wherein the catalyst comprises from about 0.01 to about 2 weight % silver based on a total weight of the catalyst.

41. The method of claim 23, wherein the catalyst comprises from about 1 ppm by weight to about 1,000 ppm by weight of iodide.

42. The method of claim 23, wherein the catalyst comprises from about 1 ppm by weight to about 800 ppm by weight of iodide.

43. The method of claim 23, wherein the catalyst comprises from about 1 ppm by weight to about 500 ppm by weight of iodide.

44. A catalyst formed by the method of claim 23.

45. The method of claim 1 wherein the alkali metal fluoride compound is potassium fluoride.

46. The method of claim 1 wherein the residual material comprises a cation of the alkali metal fluoride compound.

47. The method of claim 45 wherein the residual material comprises potassium.

48. The method of claim 23 wherein the alkali metal compound comprises fluoride.

49. The method of claim 23 wherein the alkali metal compound comprises potassium.

50. The method of claim 48 wherein the alkali metal compound comprises potassium.

* * * * *